Figure 1:
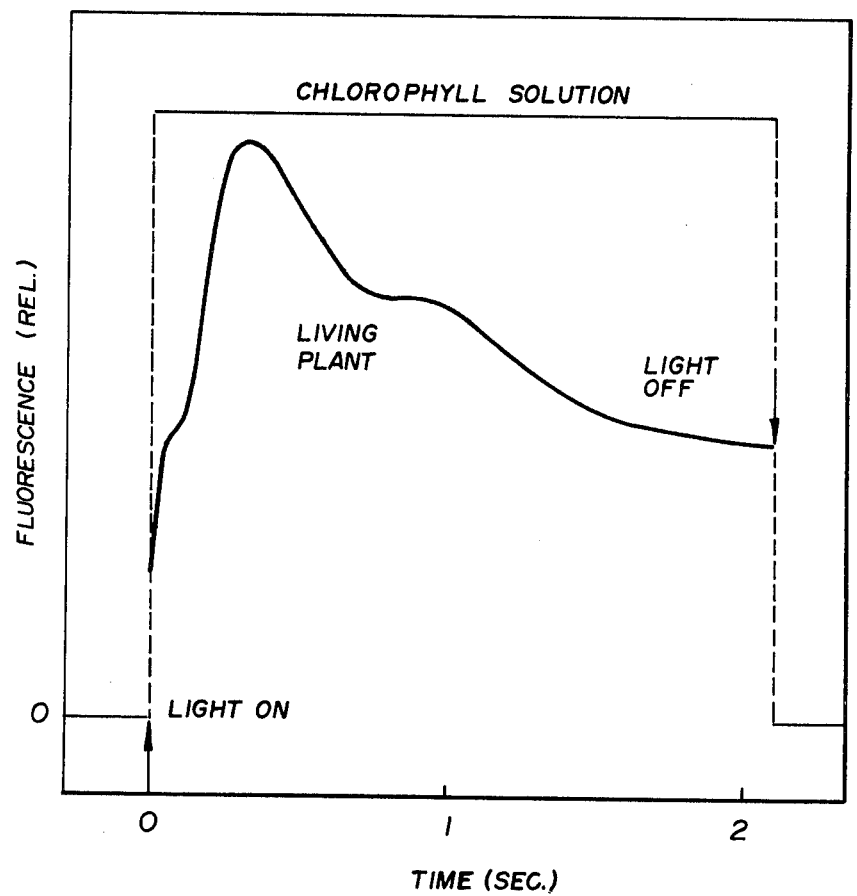

United States Patent [19]
Schreiber et al.

[11] 4,084,905
[45] Apr. 18, 1978

[54] APPARATUS FOR DETECTING AND MEASURING FLUORESCENCE EMISSION

[75] Inventors: Ulrich Schreiber, Burnaby; William Vidaver, W. Vancouver, both of Canada

[73] Assignee: Canadian Patents & Development Limited, Ottawa, Canada

[21] Appl. No.: 666,170

[22] Filed: Mar. 11, 1976

[51] Int. Cl.² ............................ G01J 3/30; G01J 3/48
[52] U.S. Cl. ..................................... 356/85; 250/458; 356/186; 356/209
[58] Field of Search ................... 356/85, 98, 209, 186; 250/458, 459, 461

[56] References Cited
U.S. PATENT DOCUMENTS

| | | | |
|---|---|---|---|
| 3,811,777 | 5/1974 | Chance | 356/85 |
| 3,910,701 | 10/1975 | Henderson et al. | 356/209 |

OTHER PUBLICATIONS

Optical Reading Wand with Multiconvex Lens; Dickson et al., IBM Tech. Disc. Bulletin, vol. 16, No. 11, Apr. 74; p. 3732.

*Primary Examiner*—Vincent P. McGraw
*Attorney, Agent, or Firm*—James R. Hughes

[57] ABSTRACT

Apparatus for detecting and measuring fluorescence emission comprising a fluorometer probe including a light emitting means for illuminating the object under study, a red cut-off filter, a light sensitive detector for obtaining the fluorscence signal from the object, and a preamplifier connected to the phototransistor for amplifying the said signal to a first level, and power and control unit including electronic indicating means. In the preferred embodiment the sensor and emitter are a light emitting diode (LED) and a phototransistor arranged in piggy-back relation with the LED having an epoxy body acting as a fluorescence light guide from the object to the phototransistor.

1 Claim, 6 Drawing Figures

APPARATUS FOR DETECTING AND MEASURING FLUORESCENCE EMISSION

This invention relates to a detector for fluorescence emission and more particularly to an apparatus for detecting and measuring the changes in the fluorescence intensity of chlorophyll in photosynthetic plants.

Rapid changes in chlorophyll "a" fluorescence intensity occur within the first moments of illumination in all photosynthetic plants. This phenomenon is known as the Kautsky effect which was described in a paper by H. Kautsky and A. Hirsch, Naturwissenschaften 48 964 (1931). This induced chlorophyll fluorescence is a sensitive indicator of photosynthetic mechanism. A standard fluorescence curve has been evolved and has been found to be modified by any factor which effects photosynthesis. Present understanding of the significance of the various fluorescence transients provides for an immediate and reliable test for photosynthetic activity. A review of these is given in an article by Govindjee and G. Papageorgiou, in Photophysiology, edited by A. C. Giese, Academic Press, New York, 1971, Vol. V1, pp. 1-46.

In a conventional "Kautsky apparatus", the measuring principle consists of the effective separation of the relatively weak fluorescence from the strong excitation light by the use of appropriate filters or monochromators. Illumination is generally controlled by a photographic shutter and the fluorescence signal detected by a photomultiplier. Among other indespensable parts are a high power lamp with its stabilized high current DC supply, a high voltage power supply for the photomultiplier, and various optical components, which for rigidity must be mounted on an optical bench. A conventional laboratory Kautsky apparatus is thus large, immobile and completely unsuited for photosynthetic field studies.

It is an object of the invention to provide a fluorescence emission detector that is light, portable, and well suited for field operation as well as sophisticated measurements in the laboratory.

This and other objects of the invention are achieved by an apparatus for detecting and measuring fluorescence emission comprising a fluorometer probe including a light emitting means for illuminating the object under study, a red cut-off filter, a light sensitive detector for obtaining the fluorescence signal from the object, and a preamplifier connected to the phototransistor for amplifying the said signal to a first level, and power and control unit including electronic circuitry for light control and signal amplification and output indicating means. In the preferred embodiment the sensor and emitter are a light emitting diode (LED) and a phototransistor arranged in piggy-back relation with the LED having an epoxy body acting as a fluorescence light guide from the object to the phototransistor.

Figure 2:
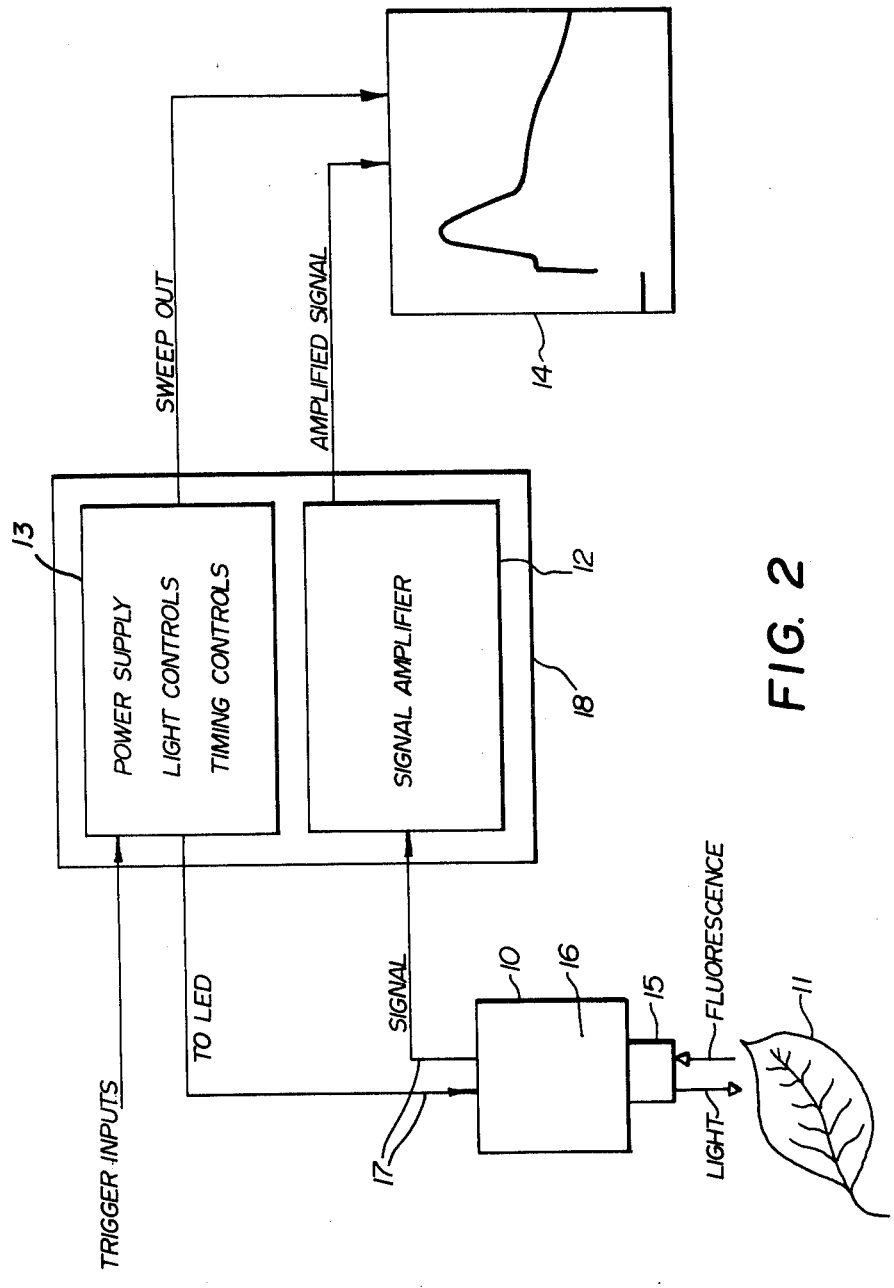
Figure 3:
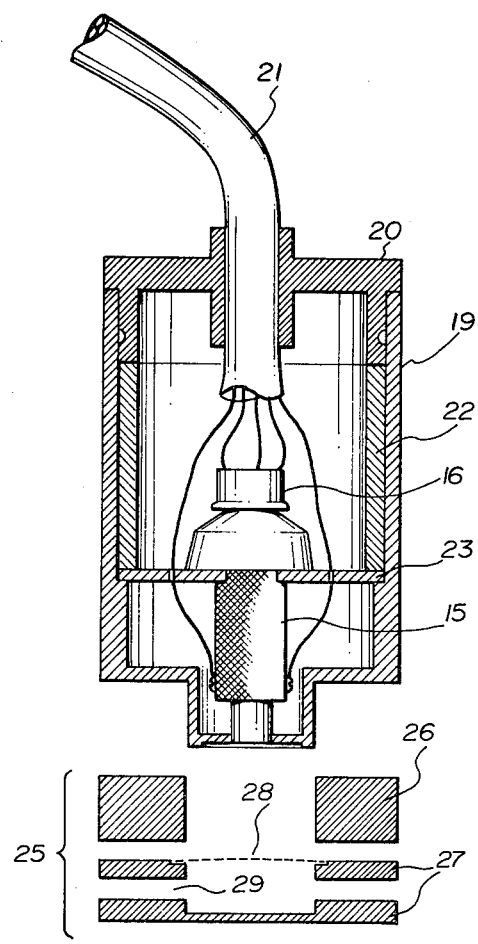
Figure 4:
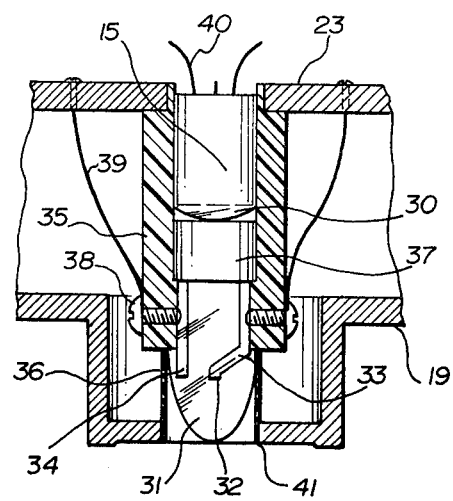
Figure 5:
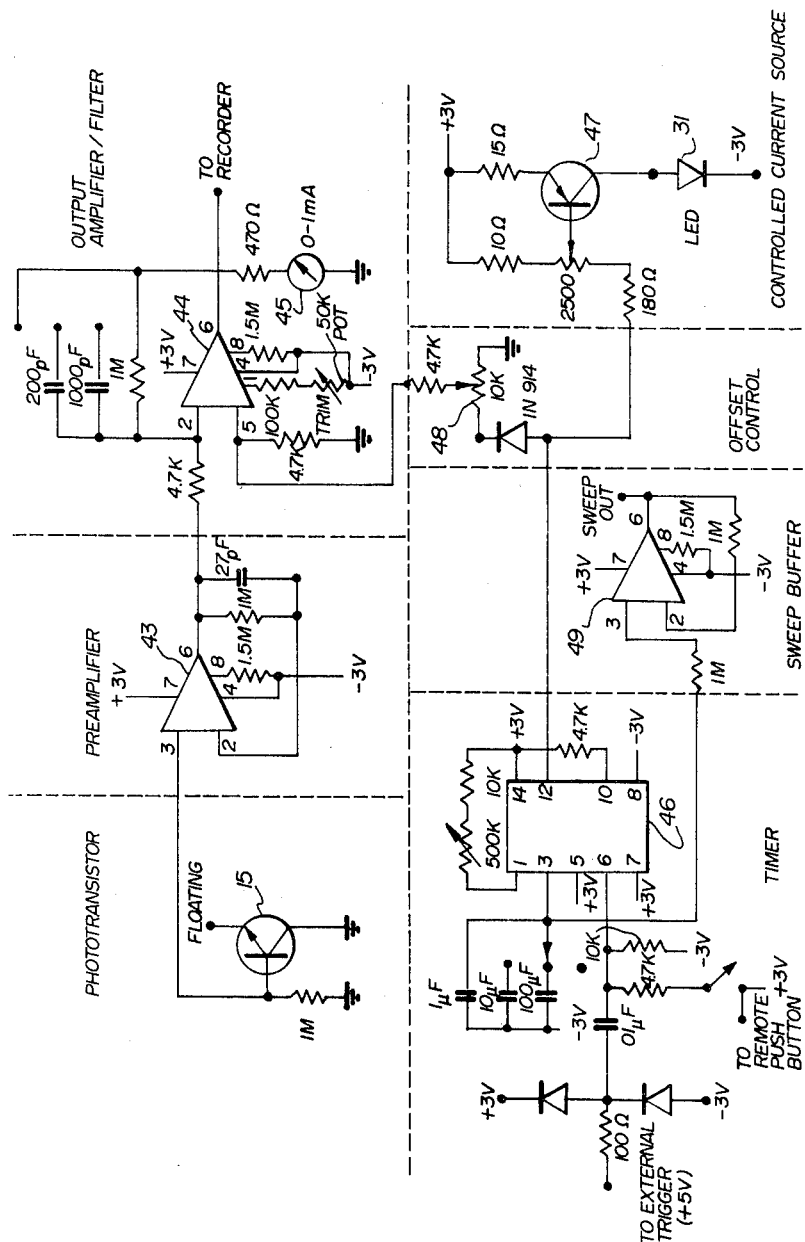
Figure 6:
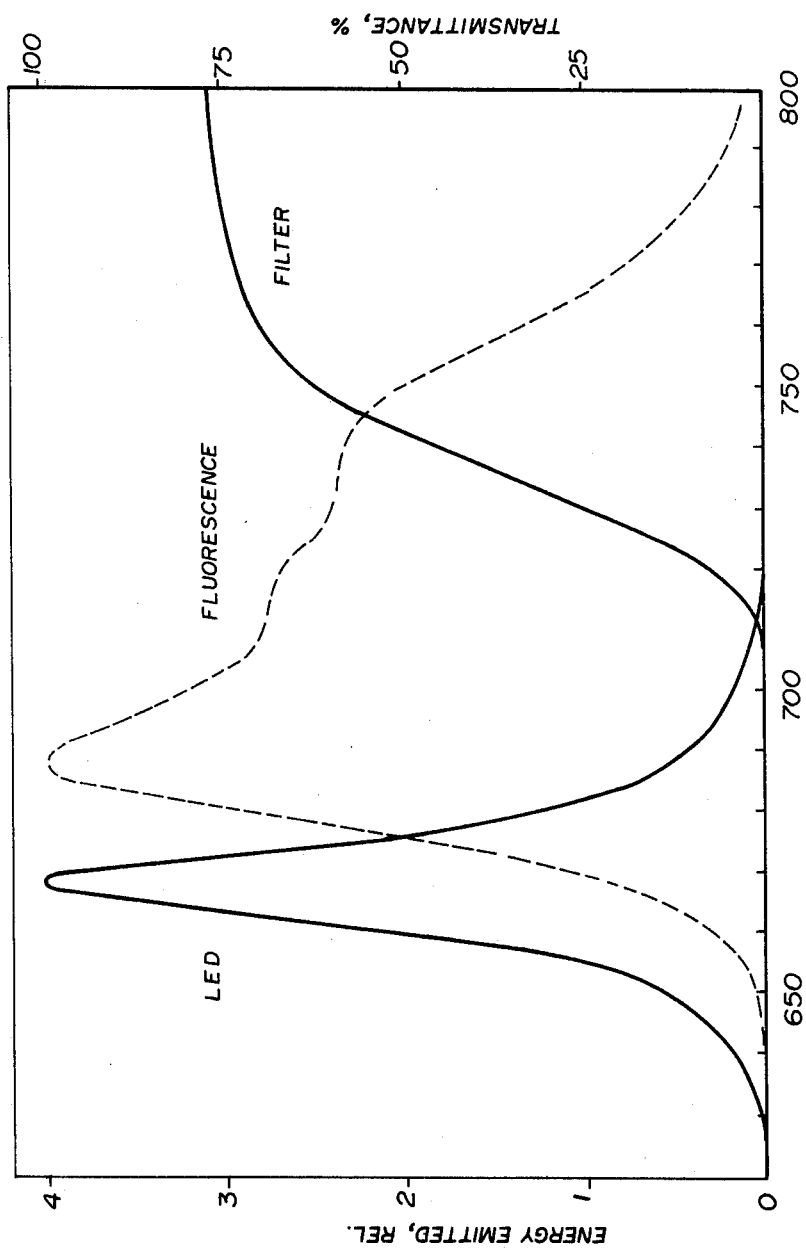

In drawings which illustrate an embodiment of the invention,

FIG. 1 is a graph showing a standard Kautsky effect curve obtained from a green plant, FIG. 2 is a block diagram of the apparatus, FIG. 3 is a cross-section of the fluorometer probe, FIG. 4 is a cross-section of the piggy-back sensor-emitter combination, FIG. 5 is a circuit diagram of the electronics for the instrument, FIG. 6 is a graph showing spectral typical characteristics of the LED and the cutoff filter in relation to fluorescence.

Referring to FIG. 1, a typical graph of the standard Kautsky effect in a photosynthetic green plant as compared to the fluorescence response of a chlorophyll solution. It is this curve that is determined by factors which affect photosynthesis and which is detected by a Kautsky apparatus for study and analysis.

FIG. 2 illustrates the overall apparatus in block form and consists of a fluorometer probe 10 positioned adjacent a sample of the object 11 under study, a signal amplifier 12, power supply, light, and timing controls 13, and an output recorder 14, preferably an oscilloscope. The probe is made up of a sensor-emitter arrangement 15 and a preamplifier 16. Leads 17 connect the probe to the main part of the instrument which is contained in a suitable enclosure 18. FIG. 3 is a cross-section of the fluorometer probe made up of a stainless steel casing 19 with cover 20, leads 21 from the main part of the instrument, a nylon sleeve 22, the sensor-emitter 15, the preamplifier 16, and a printed circuit board 23. The probe operates in conjunction with a magnet leaf holder 25 made up of a magnet ring 26, a soft steel cap 27, having opening 29 for gas exchange, a stainless steel grid 28. In use, a leaf or leaf-like sample is placed on the magnet and covered with the cap which holds the sample in place.

FIG. 4 is a more detailed cross-section of the piggy-back sensor-emitter. The core of the probe is a phototransistor 15 covered by an epoxy lens 30 and a LED embedded in an epoxy dome lens 31. The LED is made up of a light emitting chip 32 mounted on a cathode structure 33 and an anode 34. These structures are mounted inside a PVC socket 35 and black PVC tubing 36. An optical cut-off filter 37 is mounted between the LED and the phototransistor. Connections from the LED are made via screws 38 and leads 39 to the printed circuit board 23. Leads 40 from the phototransistor pass directly to the preamplifier 16 (of FIG. 3) and are made as short as possible to reduce noise pickup. A glass window 41 covers the opening in the casing allowing light from the LED to impinge directly on the sample with the fluorescence obtained from the sample passing through the epoxy lens and the cut-off filter to the phototransistor.

The piggy-back arrangement described above allows positioning of the plant sample directly over the LED ensuring maximum sample illumination and optimal collection of fluorescence. The epoxy dome of the LED collects and guides the fluorescence from the plant surface to the phototransistor. Stray and reflected incident light is absorbed by the cutoff filter which passes only wavelengths greater than 710 nm.

FIG. 5 is a diagram of suitable power and control circuitry. The phototransistor 15, an npn device is operated in the photovoltaic mode with emitter floating, collector grounded, and base circuit fed into an operational amplifier 43 selected for low noise. The photovoltaic mode provides high speed and an output current which is linear with signal intensity, neither of which is achieved in the transistor mode at the low levels of fluorescence. To obtain rapid rise times, gain of the preamplifier is kept low, with 1MΩ load on the phototransistor. Output of the preamplifier is fed to the main output amplifier and filter 44 which provides a reading to a strip-line recorder, oscilloscope, or ammeter 45 as required. A timing control circuit for controlling the operation of the LED and phototransistor comprises a variable timer 46 incorporating external trigger and remote push-button controls. The LED 31 is powered by a variable controlled current source 47. A variable voltage offset control 48 is provided between timer and the output amplifier 44. The ramp voltage from the timer also provides via sweep buffer amplifier a sweep output for an X-Y recorder.

In operation, the LED emits relatively monochromatic light with peak wavelength at approximately 670 nm. at a forward current of 50 mA. With higher currents peak wavelengths increases (to 675 nm. at 100 mA). FIG. 6 shows spectral characteristics of leaf fluorescence, LED, and filter. Because of appreciable overlap of fluorescence and incident light, only the longer wavelength fluorescence is selected, which is still sufficient to give a satisfactory signal. Rise time of the LED is in the nanosecond region and does not influence the time resolution of fluorescence measurement which is limited by the signal amplifiers.

Important aspects of performance of a Kautsky fluorometer are (a) time resolution, (b) sensitivity and signal-to-noise ratio, (c) reproducibility, (d) linearity of output signal with fluorescence signal, and (e) absence of stray light artifacts overlapping fluorescence.

Considering these aspects the described device shows the following characteristics:

(a) Time resolution is limited by speed of the signal amplifiers; rise time from 10% to 90% 250 μsec, which is faster than a conventional setup with a photographic shutter (rise time approx. 1–5 msec).

(b) Recording of fluorescence transient at low light intensity or low chlorophyll concentrations is limited by input noise (particularly low frequency flicker) at the pre-amplifier. This noise is usually negligible in recording fluorescence curves from green leaves at light intensities ranging from $2 \times 10^3$ to $10^4$ erg.cm$^{-2}$sec$^{-1}$ with characteristic signal-to-noise ratios of 10–100.

(c) Reproducibility depends primarily on the invariance with which the sample contacts the window of the fluorometer probe, given sufficient time for dark adaptation. The magnetic leaf holder assures excellent reproducibility (within 3%) by exerting gentle constant pressure on the sample.

(d) Due to use of the photovoltaic mode, the phototransistor light response is linear over the whole practical signal range of approx two decades.

(e) Analysis of the LED emission spectrum reveals at high sensitivity a long tail of emission reaching up to 900 nm (not visible at the sensitivity with which the spectrum in FIG. 6 was recorded). The tail adds up to an appreciable integrated signal as the phototransistor is sensitive in the 800–900 nm region. This stray light reaches the phototransistor by internal reflections within the LED and is essentially independent of the sample. The amount of stray light artifact thus is almost exclusively determined by light intensity. It is compensated for by adding a simultaneous "negative signal" which is adjusted for any particular light intensity by nulling the signal without a sample. This method allows the determination of initial fluorescence yield with high accuracy despite the overlap of the long wavelength LED tail.

The significant features of the present device are its compactness, portability, simplicity, and low cost as compared to a conventional Kautsky apparatus. The instrument is designed for use in the folllowing cases:

(a) Agriculture, crop science, horticulture, and forestry

It provides a rapid means for monitoring defects in photosynthetic activity due to such factors as frost, water stress, heat, disease, nutrient deficiency, or pollution.

(b) Oceanography, marine biology and marine ecology

The instrument appears superior to conventional fluorometers used in the determination of primary productivity in the sea as it can monitor time course of fluorescence and particularly initial fluorescence yield, which is a highly accurate measure of chlorophyll concentration. Prospective use is also visualized in underwater physiological or ecological studies of seaweeds and other aquatic plants.

(c) Teaching laboratories - Demonstration of the Kautsky effect is extremely helpful in teaching the principles of photosynthesis in plant physiology courses. This technique has been poorly utilized probably because of the complexity, size, and costs of the conventional Kautsky apparatus, all problems which the present instrument will solve.

We claim:

1. Apparatus for measuring light induced changes of chorophyll fluorescence yield i.e. the Kautsky effect in living plant samples comprising:
   (a) a fluorometer probe comprising:
      (1) a housing having a transparent window,
      (2) a light emitting diode mounted in an epoxy dome lens positioned inside the housing adjacent the said window for illuminating the plant sample through the window,
      (3) a phototransistor operating in the photovoltaic mode for detecting and measuring fluorescence emission received through the window from the plant sample on illumination mounted inside the housing in piggy-back relation to the said light emitting diode such that fluorescence emission from the plant sample passing through the window is collected and guided by the epoxy lens to the phototransistor,
      (4) an optical filter mounted between the window and the phototransistor,
      (5) a preamplifier adjacent and connected to the phototransistor,
   (b) timing and control means connected to the probe via an extended electrical lead cable comprising:
      (1) a timing circuit connected to the light emitting diode for controlling its on-off times,
      (2) an amplifier and electrical filter connected to the preamplifier,
   (c) output recording means connected to the said amplifier.

* * * * *